United States Patent
Winther et al.

(10) Patent No.: US 8,090,424 B2
(45) Date of Patent: Jan. 3, 2012

(54) METHOD AND APPARATUS FOR GLUCOSE LEVEL DETECTION

(75) Inventors: Dale E. Winther, Livermore, CA (US); Liming Wang, Fremont, CA (US); Runchuan Zhao, Fremont, CA (US)

(73) Assignee: STI Medical Systems, LLC, La Jolla, CA (US)

( * ) Notice: Subject to any disclaimer, the term of this patent is extended or adjusted under 35 U.S.C. 154(b) by 1200 days.

(21) Appl. No.: 11/330,406

(22) Filed: Jan. 10, 2006

(65) Prior Publication Data

US 2007/0038047 A1   Feb. 15, 2007

Related U.S. Application Data

(60) Provisional application No. 60/642,897, filed on Jan. 10, 2005.

(51) Int. Cl.
*A61B 5/1455*   (2006.01)

(52) U.S. Cl. .................................................. 600/319
(58) Field of Classification Search ........... 600/309–344
See application file for complete search history.

(56) References Cited

U.S. PATENT DOCUMENTS 5,974,521 A * 10/1999 Akerib ........................ 712/11
2005/0070772 A1 * 3/2005 Cornsweet .................. 600/319

FOREIGN PATENT DOCUMENTS

| WO | WO 00/16692 | 3/2000 |
| WO | WO 01/22061 A1 | 3/2001 |

* cited by examiner

*Primary Examiner* — Eric Winakur
(74) *Attorney, Agent, or Firm* — Martin E. Hsia

(57) ABSTRACT

An apparatus for determine a glucose level having a calibration module; an image acquisition module; an image compensation module; and, a dynamic pattern matching module. A method using the apparatus is also described.

20 Claims, 11 Drawing Sheets

G — 532nm
R — 633nm
I — 940nm

The theoretical working range for multi-wavelength glucose tracking should be the least common multiple of the working ranges of these wavelengths. The computations are based on a 2 mm cornea to iris path length and the known refractive index shift for glucose in solution.

METHOD AND APPARATUS FOR GLUCOSE LEVEL DETECTION

CLAIM OF PRIORITY UNDER 35 USC §119

The present application for patent claims priority to Provisional Application No. 60/642,897 entitled "METHOD AND APPARATUS FOR GLUCOSE LEVEL DETECTION" filed Jan. 10, 2005, and assigned to the assignee hereof and hereby expressly incorporated by reference herein.

BACKGROUND

1. Field

The present invention relates generally to detection of biological compounds, and more particularly, to a method and apparatus for glucose detection.

2. Background

In certain instances, it is necessary to measure the concentration of particular substances in a person's bloodstream. Commonly used test procedures for measuring such concentrations are invasive, requiring the drawing of blood. This can be particularly unpleasant for individuals who need to obtain concentration measurements at frequent intervals. For example, diabetic patients need to monitor the levels of glucose in their bloodstream and are required to undergo such invasive measurement procedures on a daily basis, often several times a day. Typically, the measuring is done through a finger prick to draw blood, which is placed on a test strip that is then inserted into a glucose monitoring device.

SUMMARY

In one preferred embodiment, an apparatus for determine a glucose level includes a calibration module; an image acquisition module; an image compensation module; and, a dynamic pattern matching module.

In another preferred embodiment, a method for determining a glucose level is includes capturing an image of an eye; processing the image to compensate for image capturing deviations; and, determining a match to a glucose concentration based on intensity determinations of a plurality of portions of the processed image.

Other objects, features and advantages will become apparent to those skilled in the art from the following detailed description. It is to be understood, however, that the detailed description and specific examples, while indicating exemplary embodiments, are given by way of illustration and not limitation. Many changes and modifications within the scope of the following description may be made without departing from the spirit thereof, and the description should be understood to include all such variations.

BRIEF DESCRIPTION OF THE DRAWINGS

The invention may be more readily understood by referring to the accompanying drawings in which.

Like numerals refer to like parts throughout the several views of the drawings.

DETAILED DESCRIPTION

The present invention is a glucose detection system that is able to process/analyze images taken of an eye and determine a glucose concentration.

In one preferred embodiment, the optical signals that are processed in the images analyzed in the glucose detection system are interference patterns. These interference patterns are concentric rings as would be expected using a convex lens (cornea) and a reflective flat (iris.) The changing pattern of the rings is a result of a combination of refraction, optical rotation and eye physiology with refraction being the dominant force. Image processing reveals the ring patterns when narrow contrast ranges are observed.

Preferably, the images used have similar center points. A common center point (axis) allows the algorithm to more accurately:
  i. rotate the image to the proper orientation,
  ii. adjust for pitch and yaw,
  iii. determine prime focus, and
  iv. position the detection zones for balanced measurements.

The ring patterns are dependent upon the wavelength of the light source. In one preferred embodiment, multiple wavelengths are used to resolve any ranging problem and remove subjectivity in the image processing. In another preferred embodiment, multiple wavelength combinations could be used to resolve the ranging problem. For example, two wavelengths from 0 to 390 mg/dl may be used to avoid a recurring ring pattern (an ambiguous result). Another example is using three wavelengths from 0 to 750 mg/dl. In one preferred embodiment, three wavelengths can be generated using infrared, red and green lasers.

The preferred embodiment of the camera optics design, light source type and design and algorithm are listed as follows. Specifically:
  1. Optics and Camera Design:
    a. Automatic focus
    b. Lens type and coatings
    c. Filters
    d. Lasers vs. LEDs
    e. Beam splitter or direct illumination
  2. Light Source Characteristics:
    a. Wave lengths (e.g., 532 nm, 635 nm 904 nm)
    b. Required intensity at the CCD to capture and image (e.g., 7 μW).
    c. Resulting intensity on cornea and maximum permitted allowable exposure (e.g., 14 μW; 700 μW/second)/
    d. Bandwidth of individual light sources: ±4 nm.

e. Dispersion f. Collimated

3. Algorithm Development:

a. Integrate multiple wave lengths and rings into the processing.

b. Enhance algorithm to optimize centering, detection zones and illumination c. Enhancements in procedure for establishing calibration tables.

Figure 1:
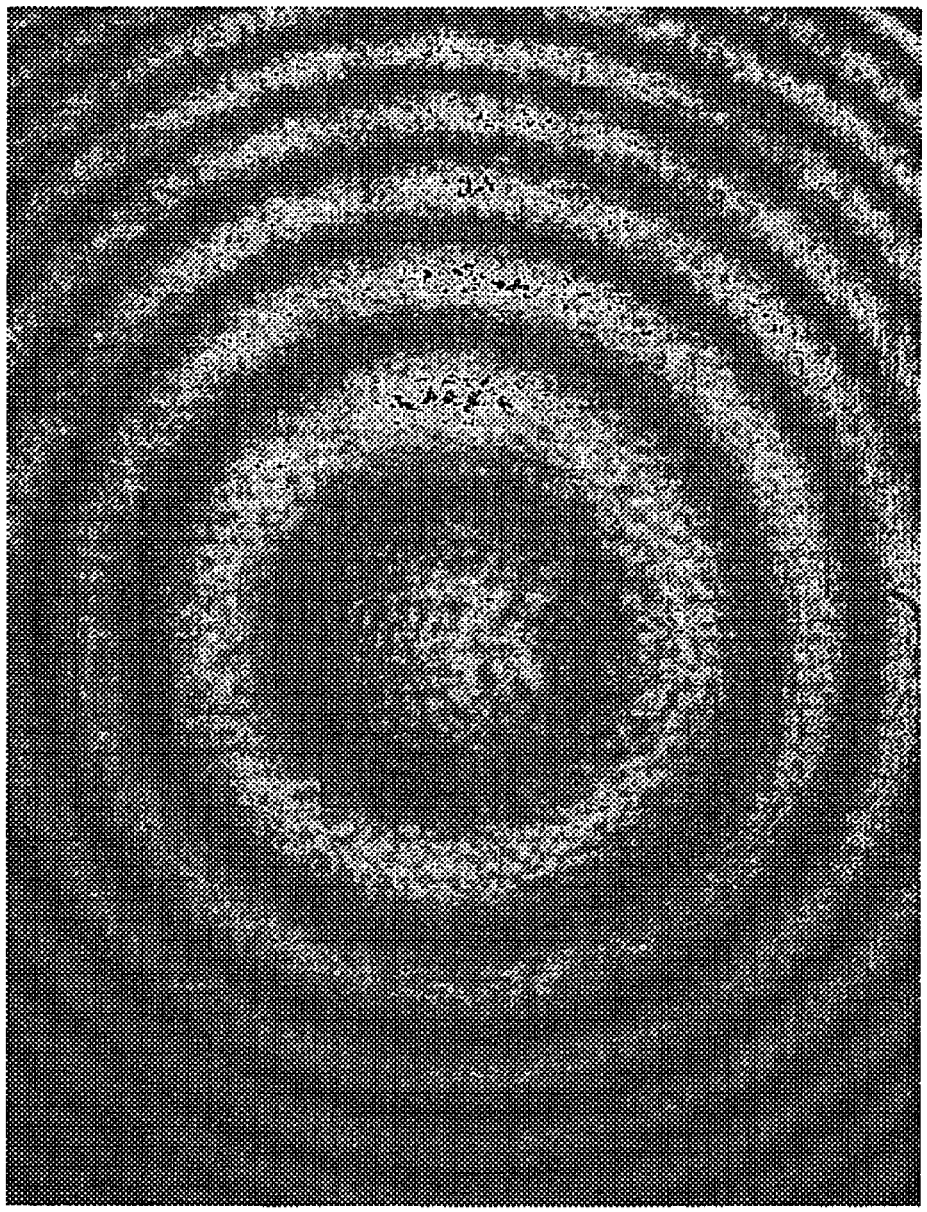
FIG. 1 illustrates ring interference patterns in an image of a human eye.

In one preferred embodiment, an artificial eye (referred to herein as the "Surrogate Eye") may be used to calibrate the system. The following exemplary description will refer to a use of the Surrogate Eye. Interference patterns change in proportion to the concentration of glucose. Further, the pattern that is observed is different for each wavelength. The fringe patterns are visible to the naked eye with lasers, extended lights sources and Sodium lamps. The interference patterns are concentric circles. Similarly, an examination of human eye images shows the same ring pattern behavior. FIG. 1 illustrates an exemplary ring interference effect, where 5 mg/dl concentration steps were used.

The interference ring patterns oscillate as the glucose concentration changes. The periodicity of the oscillation is unique for each wavelength. In one preferred embodiment, a wavelength simulation is used in attachment 1 to predict that three wavelengths (e.g., 532 nm, 635 nm and 940 nm) would resolve the ranging problem over the range of 25 mg/dl to 750 mg/dl. The simulation model assumes a narrow bandwidth (e.g., ±4 nm) light source.

Using the Surrogate Eye, experiments were conducted using infrared (904 nm) red (635 nm) and green (532 nm) lasers. The intensity of the light reaching the cornea of the Surrogate Eye was 14 µWs; with intensity of the light reaching the CCD was 7 µWs. These experiments confirmed the simulations prediction that the ranging problem can be resolved in the surrogate eye by the use of multiple wavelengths.

In one preferred embodiment, the following experiments were designed so that the optics and algorithm could be optimized:

1. The first experiment, using a green (532 nm laser) and optical flats, established the layout for observing line segment interference fringes.

2. For the second experiment, the optical flat was replaced with a cavity between two flats. The cavity was filled with various glucose concentrations. The fringe sizes, number and location changed with very small deltas in glucose concentration. The acquired images of the fringe changes could be processed by an image processing algorithm as described herein.

3. For the third experiment, the second surface in the chamber was replaced with concave and convex lens surfaces. This resulted in Newton Rings. The cavity was again filled with various glucose concentrations. The distance between the two inner surfaces of the cavity were adjusted and the rings could still be observed. Again the image could be processed with the image processing algorithm.

4. For the fourth experiment, the chamber (which we refer to as a Newton Cell) was used as the surrogate eye. A convex glass and optical flat formed the test cell. The rings were observable. The laser was still being used; however, attenuated to a power level approximately equal to that of an LED.

5. The fifth experiment replaced the laser with an extended light source (532 nm) and reverted to the chamber used in the third experiment. Again the fringes were visible to the naked eye.

6. The sixth experiment used a low pressure sodium vapor lamp (589 nm) to provide non-coherent and narrow bandwidth illumination. Fringe rings were still visible to the naked eye.

7. The seventh experiment replaced the chamber with the Surrogate Eye. Rings were still visible to the naked eye.

8. In the eighth experiment, a 3 wavelength LED and the Surrogate Eye images were acquired from 0 mg/dl to 171 mg/dl glucose concentrations. Processing the images revealed the ring patterns and the same relationship among the wavelength as recorded with the lasers.

9. The ninth experiment illuminated a living fish eye with a green laser. Rings were observed with the naked eye.

The positioning of the detection zones in four quadrants of each image in the processing algorithm was capturing the changes in the rings caused by concentration changes. In the Surrogate Eye experiments, there exist properly aligned and centered images. The primary phenomenon that is observed is changes in interference ring fringes related to the changes in the refractive index as the glucose concentration increases. Secondary effects include the change in amplitude of the rings along the Z-axis and potentially some optical rotation within the image.

Attachment 1 is a companion description of how the glucose response in the human eye image is detected. In one embodiment, imaging glucose measurements have been achieved that can resolve concentrations changes on the order of 5 mg/dl.

Figure 2:
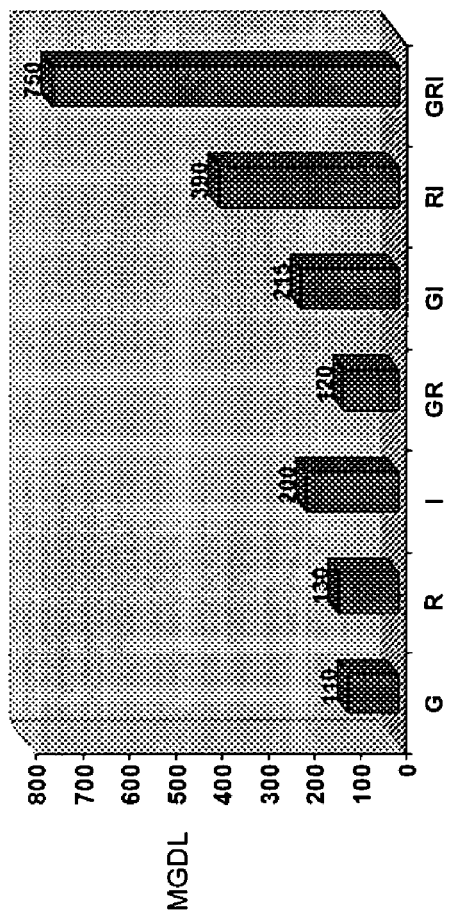
FIG. 2 illustrates the concentration range measurement limitations with specific combinations of wavelengths.

The issue of wavelength periodicity is explored as a method of preventing ranging errors in the imaging measurement system. In one preferred embodiment, a computer simulation was performed to map the sinusoidal relationships between a set of wavelengths and the change of glucose concentration for a specific path length between the cornea and iris. The simulation predicts that it is possible to resolve glucose concentrations up-to at least 750 mg/dl using three wavelengths. FIG. 2 is a chart that indicates the concentration range measurement limitations with specific combinations of wavelengths.

In preferred embodiment, validation was performed using lasers, an extended light source and a sodium lamp. These methods of illumination all showed visible rings. In contrast, where an instrument uses LED's for illumination, the narrow illumination cone and larger bandwidth of an LED typically precludes the observation of rings with the un-aided eye.

Newton ring effect should be present but not readily visible when an LED is used as a light source as the rings should have very poor contrast and overlap. In one preferred embodiment, two methods were used to confirm the presence of these rings in the image data.

1. Polynomial plots from the phase detection bars over the images. These plots look the same as the polynomial plots from the visual ring waves produced by the lasers. These plots also track the periodicity of laser produced ring waves relative to the laser and LED wavelengths.

The Surrogate Eye was used to perform the laser and LED glucose imaging experiments. The cornea to iris path length was set to approximate the distance used in the periodicity simulation.

Glucose concentrations were increased by adding 0.2 cc drops of concentrated glucose water to the surrogate eye reservoir between the cornea and iris. The solution was allowed to diffuse over a 1 minute period before taking the next concentration image.

Figure 3:
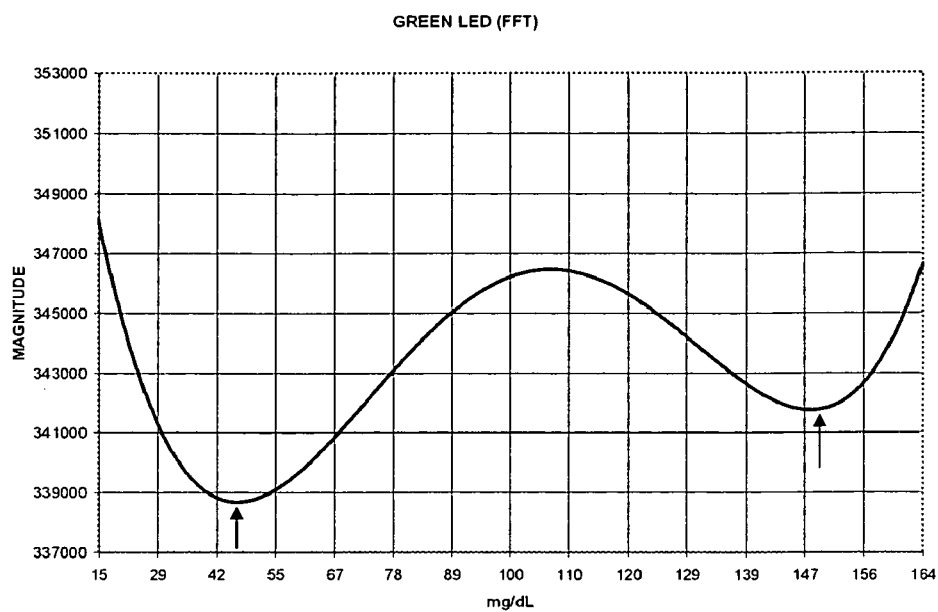
FIG. 3 illustrates trend line plots for images taken with green illumination devices over similar concentration ranges.
Figure 3:
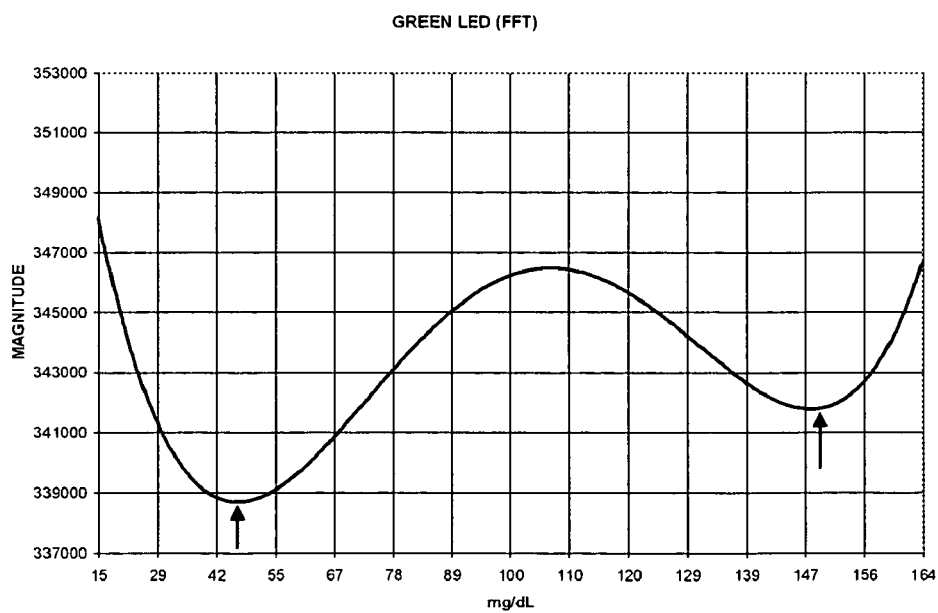

FIG. 3 illustrates the trend line plots for the green laser and the green LED over similar concentration ranges. The laser has a trough at 88 mg/dl and a peak at 153 mg/dl for a half cycle of 65 mg/dl. The LED shows a complete cycle with the first trough at 42 mg/dl and the second trough at 147 mg/dl. This is 105 mg/dl. If the trend line interpretation includes the next point of 156 mg/dl the result would be 114 mg/dl. The theory predicted 110 mg/dl for a full cycle so both the laser and the LED are very close to the prediction.

Figure 4:
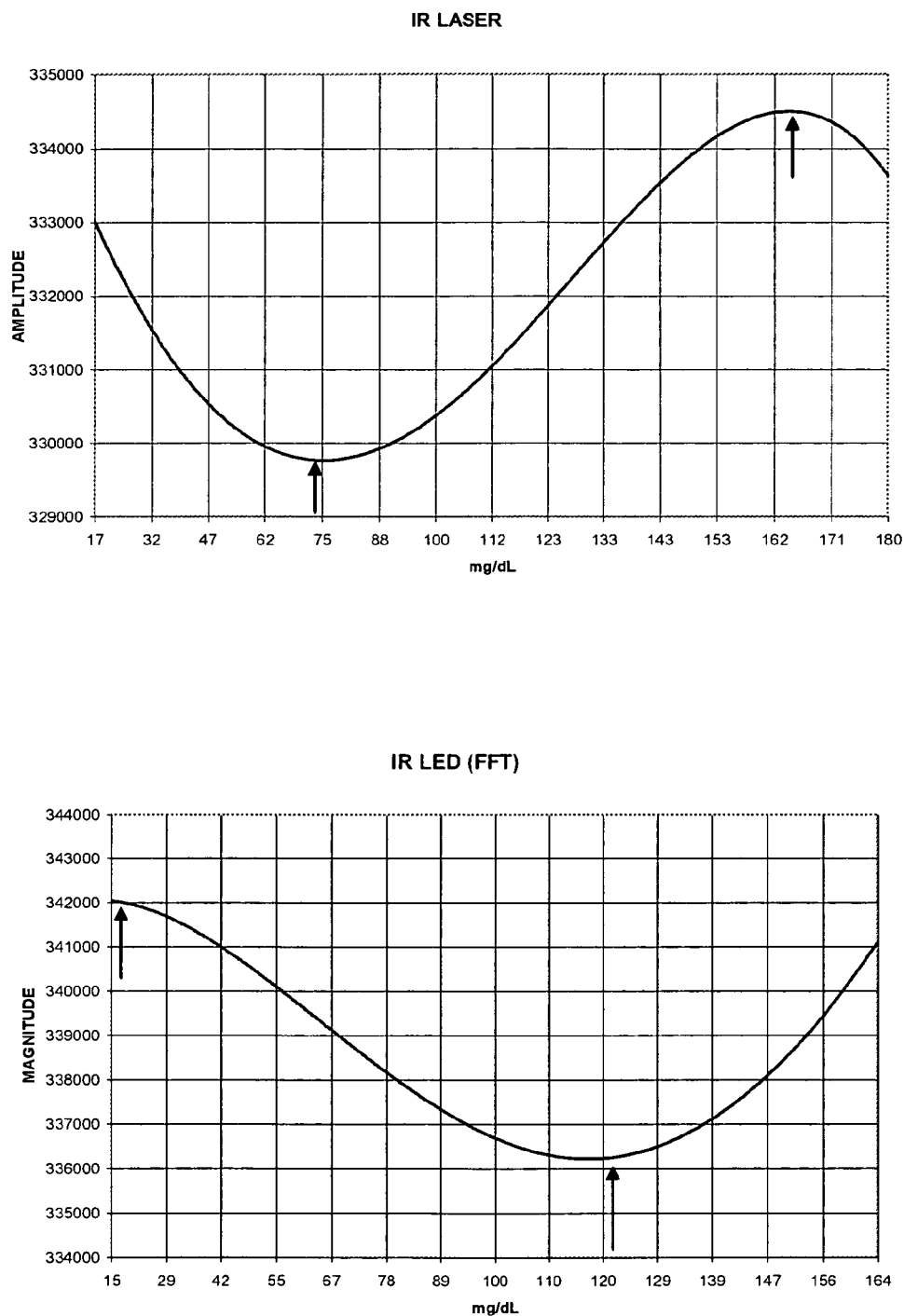
FIG. 4 illustrates trend line plots for images taken with infrared illumination devices over similar concentration ranges.

FIG. 4 shows the trend line plots for the infrared laser and the infrared LED. The laser has a trough at 62 mg/dl and a peak at 162 mg/dl for a half cycle of 100 mg/dl. The LED has a peak at 15 mg/dl and a trough at 120 mg/dl for a half cycle of 105 mg/dl. The theory predicted 200 mg/dl for a full cycle so both the laser and the LED are very close to the prediction.

Figure 5:
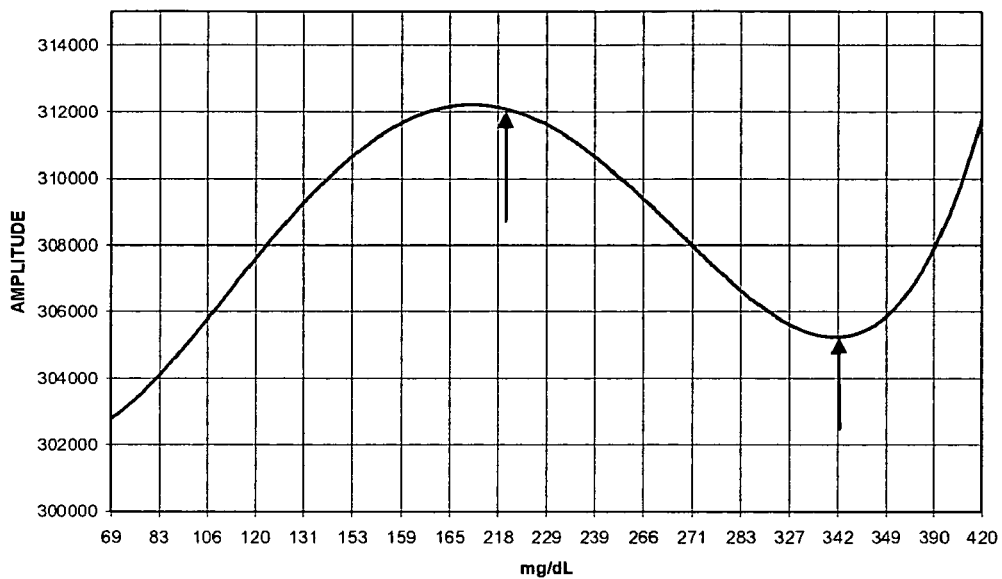
FIG. 5 illustrates trend line plots for images taken with green and infrared illumination devices over similar concentration ranges.
Figure 5:
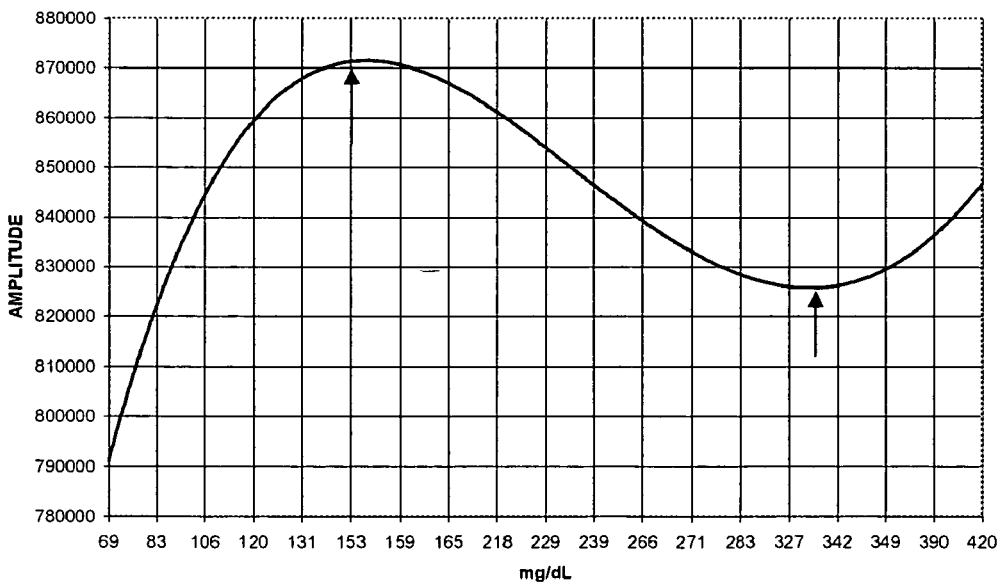

FIG. 5 compares the trend lines for green and infrared LED illuminated images of a type 1 diabetic (referred to as Walter). The cornea to iris path length was not known but the results obtained suggest an approximate 2:1 difference in path length between the surrogate eye and the human eye. The purpose of the human comparison is to show that the relative periodicity per wavelength is similar to the surrogate eye.

The trend line plots for the infrared LED show a peak at 131 mg/dl and a trough at 327 mg/dl for a half cycle of 196 mg/dl. The trend line plots for the green LED shows a peak at 218 mg/dl and a trough at 342 mg/dl for a half cycle of 124 mg/dl. Allowing for trend line interpretation error the relative periodicity differences between infrared and green results in the human subject confirm that these results are quite close to the periodicity ratios predicted by the theory and the surrogate eye measurements.

Figure 6:
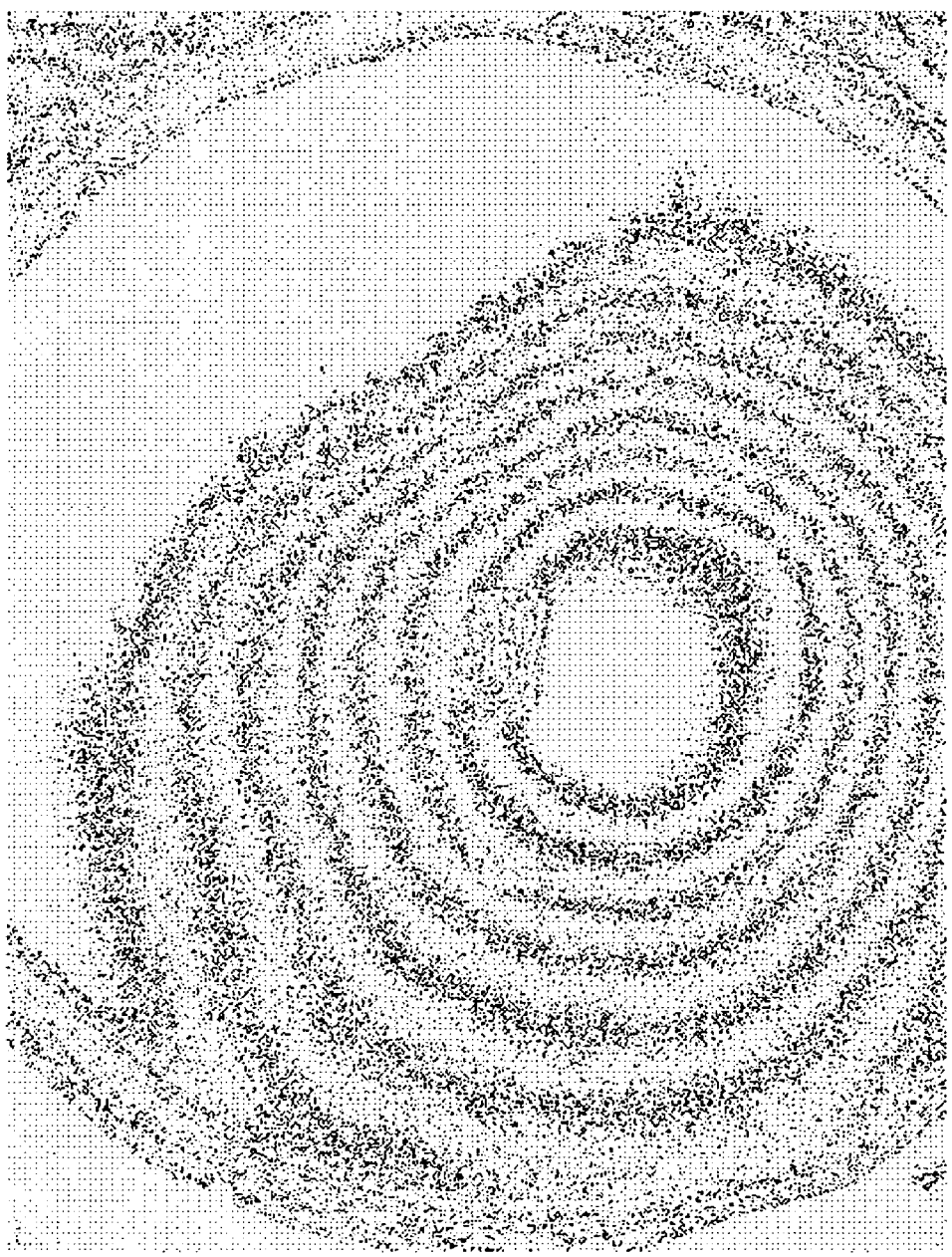
FIG. 6 illustrates ring bundles embedded within a surrogate eye image.
Figure 7:
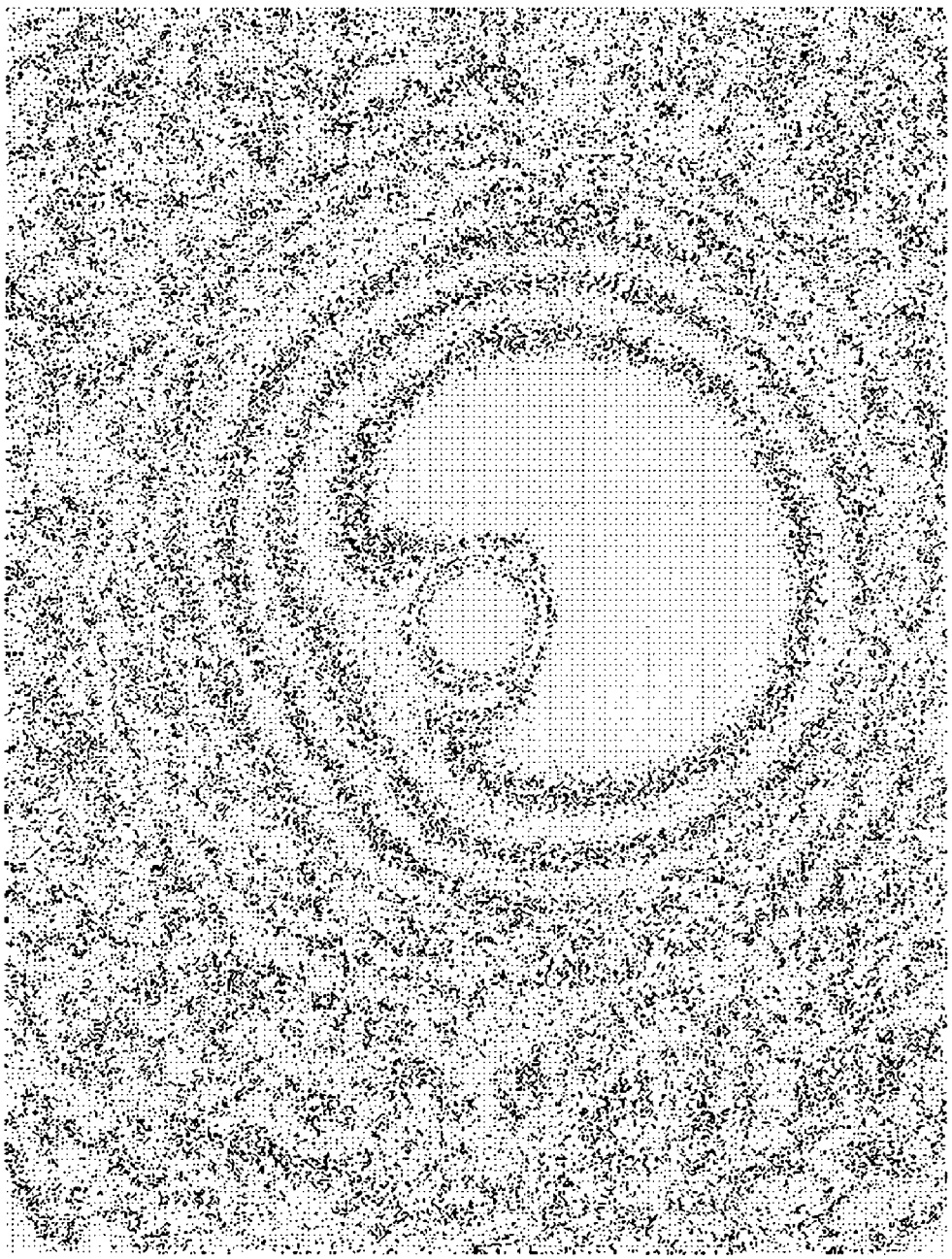
FIG. 7 illustrates ring bundles embedded within a trial subject image.

2. Bundles of overlapping rings are visible after processing in the surrogate eye and human eye images. FIG. 6 shows the ring bundles embedded within the surrogate eye image (captured with LED illumination). FIG. 7 shows the ring bundles in a trial subject image (T001).

Ring bundles are recovered from the surrogate and human eye images using an image-processing method called "Contrast Layering", where, in one preferred embodiment, very small contrast ranges are stretched (equalized) to make them visible. For example, if the dynamic range of the image is contained within 8 bits then 256 gray levels can be seen. When a small contrast range like 40-42 is stretched to 0-255 a ring appears at a specific radius from the center of the image. 50-52 shows a ring at a different radius, etc. Contrast rings are collected from the entire dynamic range of the image producing multiple sub-images. These sub-images are added together to produce a montage (composite) showing all of the ring bundles within a single image.

Montage images for different concentrations show variations in ring bundle width, brightness and position that directly account for the signal response at the phase detectors in the software. Ring wave action using the LED source is not as dramatic as the response obtained with a laser. The ring wave action is, however, visually observable with concentration changes.

Ring wave behavior is embedded within the eye images and the phase detector is able to detect them due to the inherent sensitivity afforded by doing ratios of large integrated spatial regions of the image.

Figure 8:
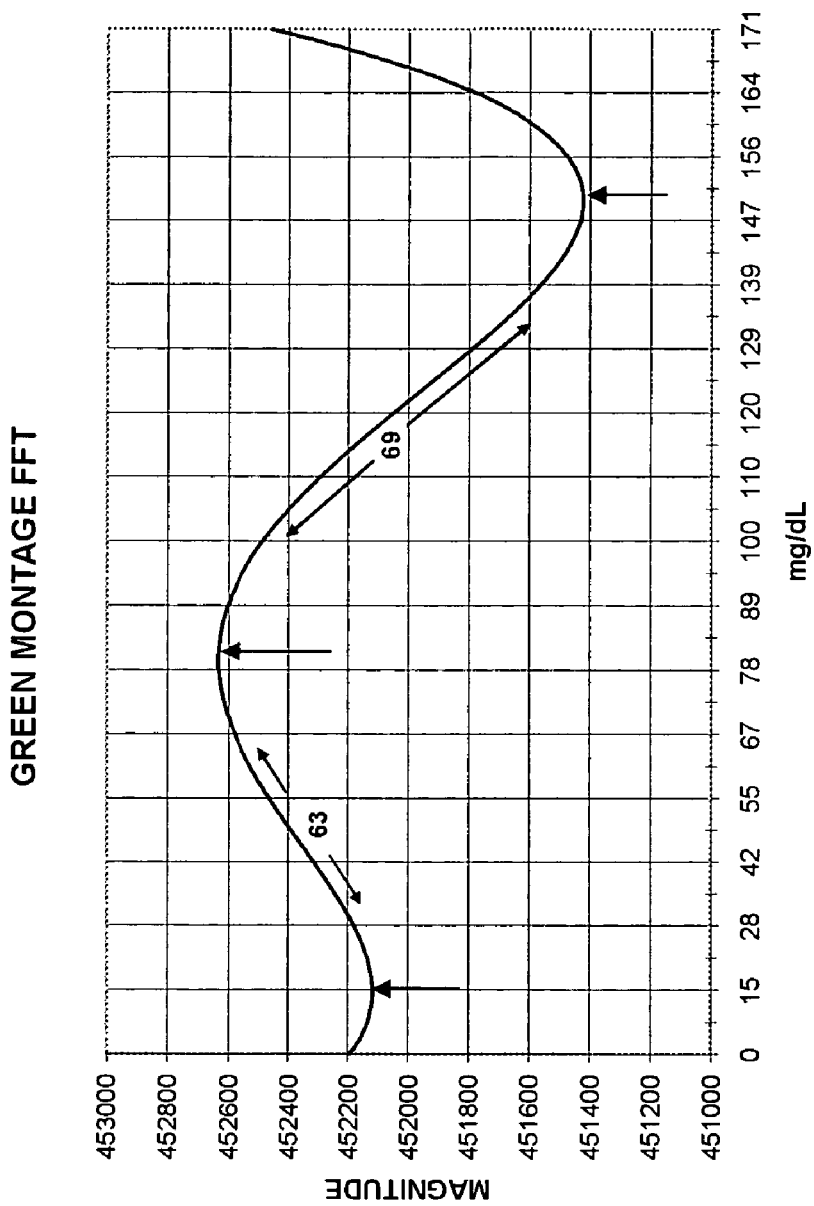
FIG. 8 illustrates a trend line plot for a green LED ring montage.

FIG. 8 shows the trend line plot for the green LED ring montage. The first half cycle is 63 Mg/Dl and the second half cycle is 69 Mg/Dl. The theoretical model predicted 55 Mg/Dl per half cycle. This result is well within the expected accuracy margin for the measurement. This significance of this result is that the plot was performed using only the ring data from the images. The other image information was excluded, demonstrating that the glucose signal detection from the complete image is in accord with the embedded ring pattern response.

Ring wave motion across "L" shaped phase detector (i.e., Image areas analyzed in our system is in the shape of the letter "L"—thus, the vertical and horizontal pixels are in the shape of an L. In other embodiments, other shapes may be used) accounts for the different ratios represent different concentrations of glucose. The image position must be repeatable and the phase detectors must be fixed relative to the center of the ring field.

The algorithm rotates the image to find the best phase matching. In one embodiment, the ring axis is off-center. This arrangement produces an asymmetric ring mapping function as the image is rotated. Segments of different rings and their spatial relationships are followed. Phase pattern matching between images during the rotary process yields the lowest standard deviation when the best fit is achieved.

In one embodiment, trial images were captured and processed with off-center axis positioning. This was done to permit alignment using the bright spot from the LED. If the LED shines directly into the center it cannot be seen in the image due to the shadow from the back side of the LED package.

Rotating the image when the axis is at the exact center of the image will restrict the processing to a single ring set. With good ring symmetry the rotation process will not yield a difference between rotary positions.

Figure 9:
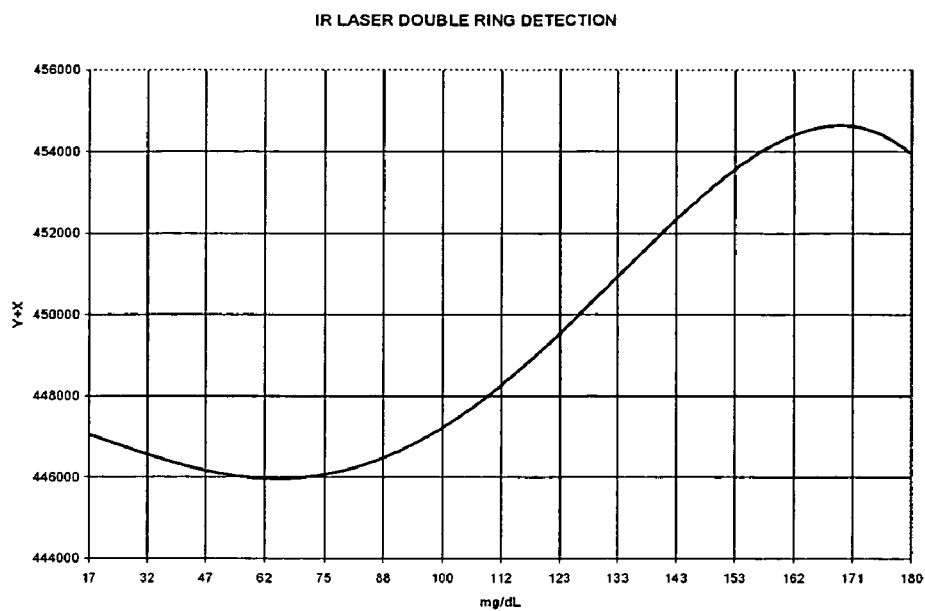
FIG. 9 illustrates the use of a spatial differential that reduces the impact of ancillary brightness variation.
Figure 9:
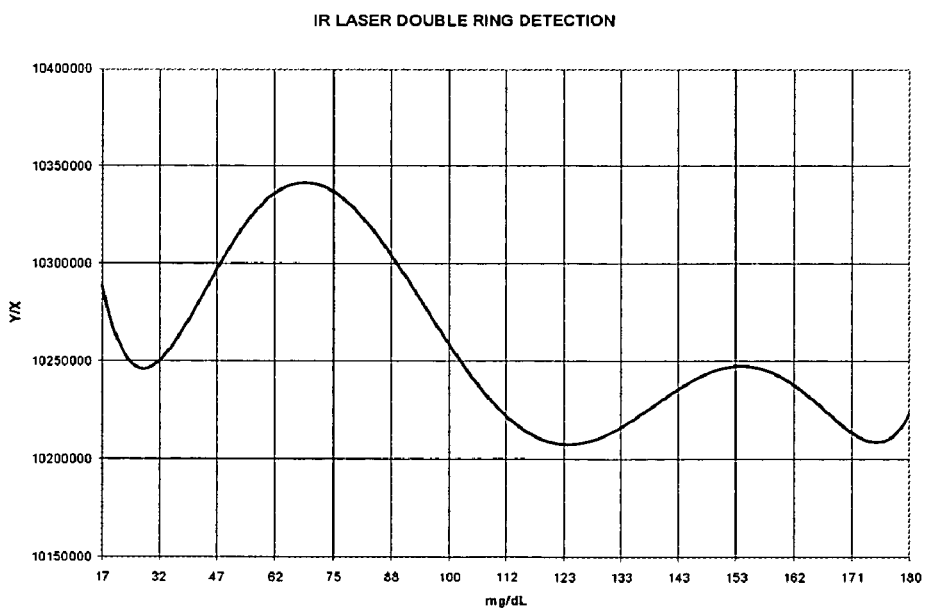

In one preferred embodiment, signal detection can be performed by tracking the amplitude from Y+X of the L shaped phase bars. The technique of using the ratio of Y/X produces a spatial differential that reduces the impact of ancillary brightness variations. The ratio method is very sensitive to the detector positioning. FIG. 9 demonstrates the issue using a green laser. The C detector period plot is correct for amplitude. The C detector period plot for phase shows that the period of the phase is about twice the period of the amplitude.

The approach of the ring wave across the L shaped detector can produce a leading and trailing ratio when the ring pattern crosses the detector at an angle because of the differential measurement. The amplitude measurement only responds to the ring passing and cannot detect the ring edges. This situation accounts for the observation during the processing of some trial images that two matching peaks are present during image rotation.

In one preferred embodiment, the ring axis relative to the detection zones is fixed. All images should be pre-processed to locate the axis at the same relative location.

In one preferred embodiment, a technique of "Hyper Centroiding" is performed prior to capturing images. Each frame is repositioned by shifting the X and Y orientation of the image until all of the images are at the same place. Doing a contrast stretch between 254 and 255 locates the brightest point in the image which is at the center of the LED reflection spot. This centroid calculation is very accurate because only the light spot is considered in the computation. The resulting "hyper centroid" defines the axis point for the ring series.

The sensitivity afforded by doing phase ratios has the advantage of making differential measurements while minimizing the impact of uneven and stray light across the image. The disadvantage is that detector orientation may be critical and ratios may be upset by the presence of uneven image features.

Figure 10:
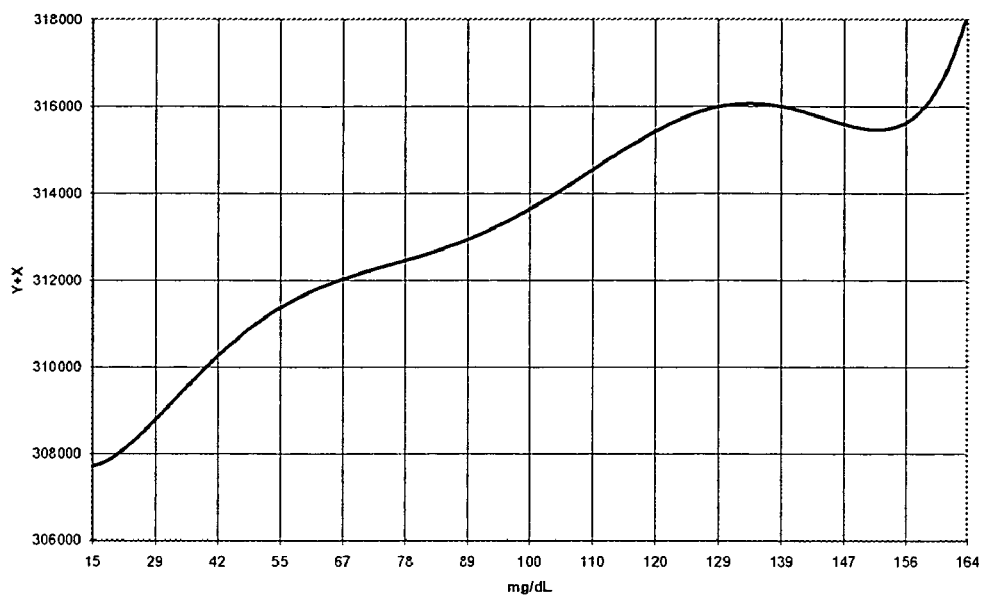
FIG. 10 illustrates an amplitude plot of an image captured using a green LED as illumination; and, FIG. 11 illustrates an image of the surrogate eye illuminated with a green LED.
Figure 10:
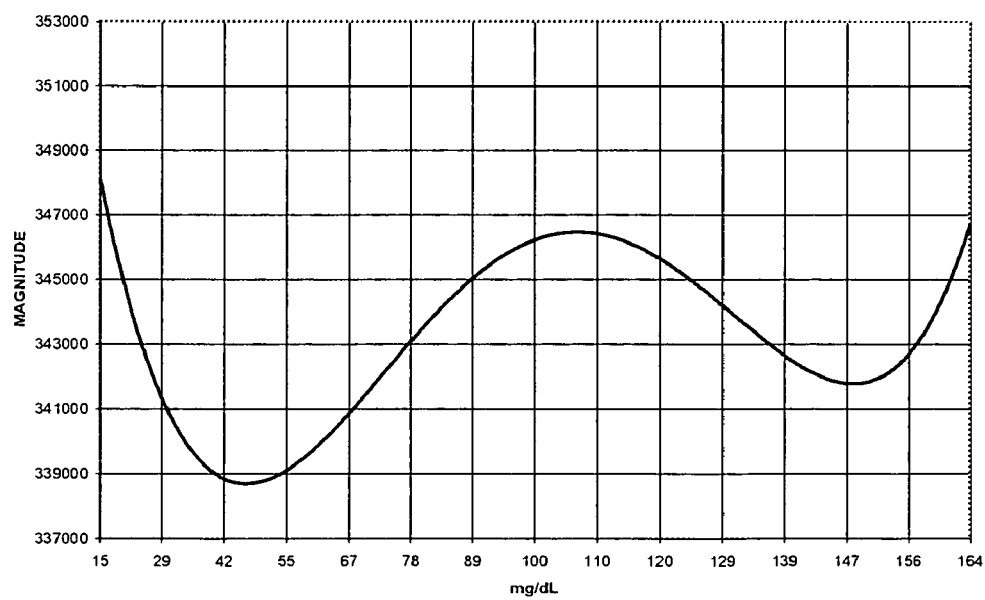
Figure 11:
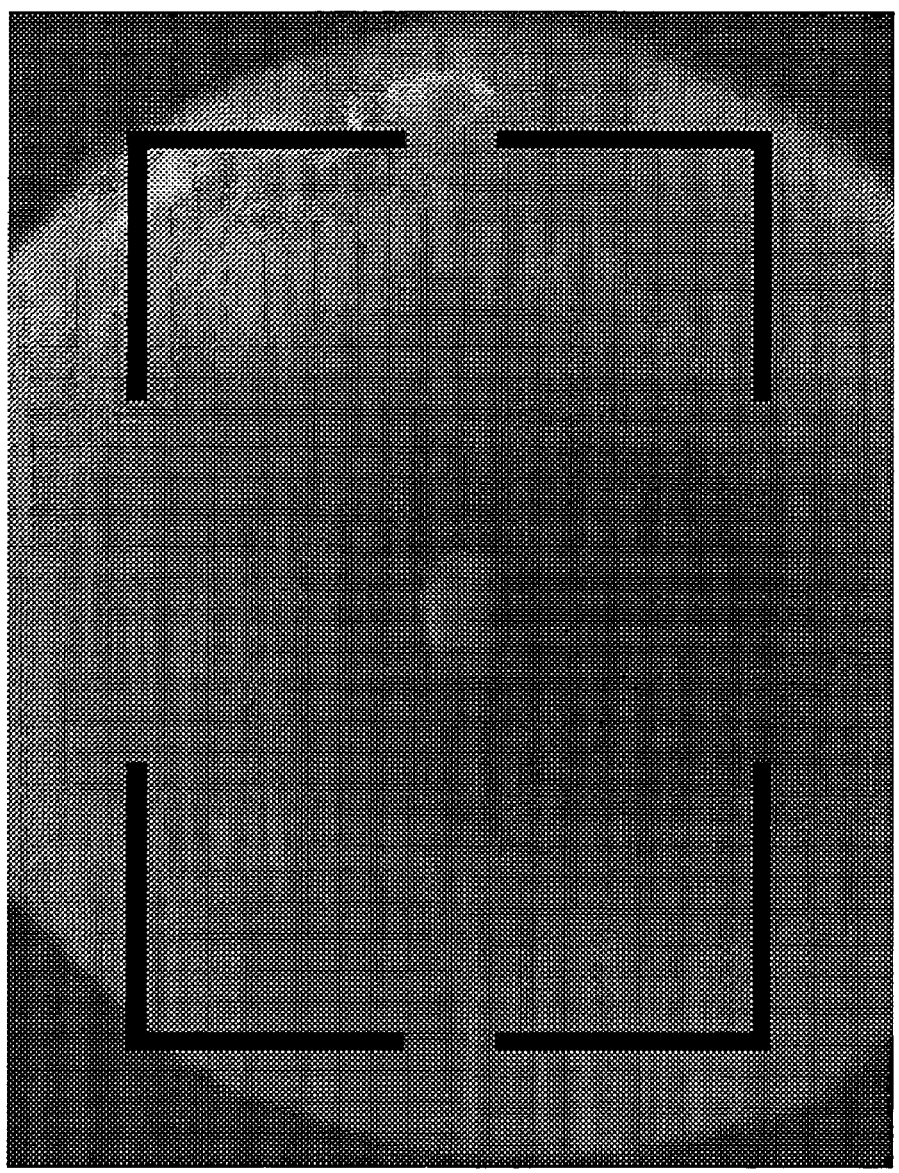

In another preferred embodiment, the application of a two-dimensional Fourier transform is used instead of the phase detection method described above. FIG. 10 shows the amplitude plot of the green LED. The plot is weak in dynamic range and disturbed by the fact that the C phase L elbow overlaps the active image border (FIG. 11). FIG. 10 also shows the plot after the application of the Fourier transform. The elbow distortion is removed and a better plot is produced. Immunity to uneven and stray illumination problems is actually better than the differential measurement rationing technique.

In another preferred embodiment, another algorithm enhancement for confirming the measurement accuracy is the application of a multi-frequency band Fourier transform. Experiments demonstrate that the human subject's glucose could be tracked using a calibration table produced from the surrogate eye and sugar water. This was done using a multi-frequency band Fourier transform. The process has been repeated using the Surrogate Eye with good success (SE to SE measurement comparison).

Newton ring widths become smaller as the radius of the ring wave increases from the center. This may explain why the multi-frequency band transform works well. A Fourier transform isolates the different ring widths and maps the different spatial frequencies. This process allows the algorithm to confirm the relationships between ring sizes and further improve the glucose estimation accuracy.

The integration of three wavelengths into the estimation algorithm is straight-forward. Images for each wavelength are processed independently. A list of the best 3 matches for each wavelength is compared. Correlating the closest concentration estimations among the three wavelength responses will resolve the ranging.

Eye motion is extreme when illumination colors are switched. In one preferred embodiment, the camera used to capture an image is capable of simultaneous multi-wavelength illumination and capture.

The existing algorithm and proposed enhancements are not light source dependent. The primary advantage of using laser light is a significant improvement in the signal-to-noise ratio. Well defined high contrast rings will replace low contrast ring bundles. The ring contrast is substantially better due to the narrow laser bandwidth.

The experiments with laser detection have been performed with the laser beam spread-out to cover the field of view. This configuration does not project a central axis bright spot like the LED. The central axis must be optically produced for the hyper centroiding procedure to work.

In an alternate approach to locating the central axis, a hypothetical axis from the interior circumference of the thickest ring is calculated. This ring is always the inner most ring of the ring sequence.

Good ring contrast can improve statistical processing. The rotation of the trial image against the calibration image parameters presently produces a single standard deviation result for the rotation matching sequence. For example, the effectiveness of multipoint pattern matching with LED illumination is reduced during the image rotation matching sequence due to noise induced tracking uncertainty. With better ring contrast, the multipoint (pattern matching for all steps in the rotation) deviation tracking should enhance the estimation reliability.

The current version of the processing algorithm consists of software modules that are linked together. These modules are:

I. Calibration Module
  a. Setting Base Image Parameters
    i. Pupil Diameter
    ii. Position and orientation
  b. Imaging, using base image parameters, at various glucose levels. Glucose levels are confirmed with finger sticks other tests.
  c. Detection Zone ratios are calculated for each zone for each concentration for each wavelength.
  d. The results are related to the known sine curve relationships of the wavelengths to interpolate between the calibration points and to extrapolate above and below the low and high calibration points, respectively.
  e. The images and the sine curve equation constitute the unique Calibration Table for the individual.

II. Image Acquisition Module: Matching the Base Image Parameters
  a. Center the light spot to the detection zones.
  b. Pupil: Diameter and Centering
    i. Centering-manual to be replaced with targeting system.
    ii. Diameter of pupil is manipulated using light in the left eye.
  Preferably, the right eye must have a sympathetic response to light and movement in the left eye.
  c. Orientation—Pitch and Yaw
  d. Focus: the lens is set at a wide-open aperture (e.g., f1.4), which results in a very shallow depth of field. The current manual focus makes it difficult to establish a repeatable focal point.

III. Image Compensation Module: The image acquisition module acquires an image as close as possible to the Base Image Parameters and compensate for image capture parameter deviations. The Image Compensation Module processes the images to better fit the Base Image Parameters.
  a. Orientation and contrast
  b. Alignment: The image is aligned such that the detection zones are equidistance from the center spot of the pupil.
  c. Brightness/Amplitude
    i. Auto ranging on brightness
    ii. FFT (Fast Fourier Transform)
(In one embodiment, at this point, the image is ready for processing into an mg/dl reading.)

IV. Dynamic Pattern Matching Module
  a. The image is rotated around the axis (center point of the detection zones and concentric rings) from −3° to +3° of TDC in 0.1° increments providing 61 points for comparison.
  b. Each point is compared to the Calibration Table for the Best Fit. Best Fit means the closet ratio proximity of 3 of the 4 quadrants to the Calibration Table ratios.
    i. The Best Fit match is done for each wavelength.
    ii. The ratio is the sum of the pixel intensity on the horizontal detection bar divided the sum of the pixel intensity on vertical detection bar. There are 1500 pixels in each bar.
    iii. As the glucose concentration increases, the ratio increases to a crest and then starts declining to a trough, following the trough the ratio increases back to the crest point. For a 635 nm wavelength illumination source, the glucose concentration changes approximately 120 mg/dl from crest to crest. Thus in a range of 360 mg/dl there could be 3 points that yield the same ratio and this causes ambiguity. Fortunately, the change in mg/dl from crest to crest is different for each wavelength. The ambiguity of multiple answers can be resolved with multiple wavelengths. While the algorithm would process the three answers for each wave length, for a total of nine (9) possible answers in the example, there would only be one common answer among the three wavelengths.
    iv. The algorithm picks the common answer.

In one preferred embodiment, the algorithm is automated and does not require external intervention. In another preferred embodiment, the algorithm allows for input by a user at several stages in the processing. Manual input allows the user to follow the calculations and observe the many parameters that are being calculated. Manual intervention may occur at:

1. Setting the base image parameters.
2. Inputting glucose readings during calibration visit.
3. Image acquisition is automatic; however, since there is no focus, there is a manual override in the event that the patient is having difficulty.
4. Image selection for the calibration table has a manual override.
5. Resolving ambiguity is manual.

It should be noted that the methods described herein may be implemented on a variety of hardware, processors and systems known by one of ordinary skill in the art. For example, the general requirement for the client to operate as described herein is that the client has a display to display content and information, a processor to control the operation of the client, a camera to capture images, an illumination system for illuminating the eye, and a memory for storing data and programs related to the operation of the client. In one preferred embodiment, the client is a handheld computer. In another preferred embodiment, the client is a personal computer. In yet another preferred embodiment, the client is a cellular phone. In addition, hardware such as a communication interface may be incorporated as necessary in the client to implement the various embodiments of the present invention. The various illustrative logics, logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, a hard disk, a removable disk, a CD-ROM, or any other form of storage medium known in the art. An exemplary storage medium is coupled to the processor, such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

The embodiments described above are exemplary embodiments. Those skilled in the art may now make numerous uses of, and departures from, the above-described embodiments without departing from the inventive concepts disclosed herein. Various modifications to these embodiments may be readily apparent to those skilled in the art, and the generic principles defined herein may be applied to other embodiments, e.g., in an eye diagnostic device or any general medical diagnostic application, without departing from the spirit or scope of the novel aspects described herein. Thus, the scope of the invention is not intended to be limited to the embodiments shown herein but is to be accorded the widest scope consistent with the principles and novel features disclosed herein. The word "exemplary" is used exclusively herein to mean "serving as an example, instance, or illustration." Any embodiment described herein as "exemplary" is not necessarily to be construed as preferred or advantageous over other embodiments. Accordingly, the present invention is to be defined solely by the scope of the following claims.

What is claimed is:

1. An apparatus for determining a glucose level of an individual, comprising:
a processor configured to execute modules comprising:
a calibration module configured to produce a calibration table created by analyzing a plurality of portions of Newton's Rings in images from a calibration eye at multiple wavelengths obtained at various glucose levels, using first base image parameters, said calibration module configured to store said calibration table in a storage medium;
an image acquisition module configured to receive captured images of a plurality of portions of Newton's Rings in an eye of said individual at said multiple wavelengths from means for capturing images, using second base image parameters that approximate said first base image parameters;
an image compensation module for compensating the captured images for differences between said base image parameters; and
a dynamic pattern matching module for comparing points on said plurality of portions of Newton's Rings from said compensated captured images to corresponding points in said calibration table at said multiple wavelengths to determine various possible concentration values for each wavelength, and for determining one common answer from the various possible concentration values as said glucose level of said individual.

2. An apparatus according to claim 1, further comprising at least one light source providing light at multiple wavelengths selected from the group consisting of lasers, light emitting diodes, sodium lights, extended light sources, and light with filters.

3. An apparatus according to claim 1, wherein said points comprise L "L" shaped phase detector areas.

4. An apparatus according to claim 1, wherein said processor controls operation of a client, and said client further comprises a display to display content and information, a camera to capture images, an illumination system for illuminating said individual's eye, and a memory for storing data and programs related to the operation of the client, wherein the means for capturing images is the camera.

5. An apparatus according to claim 4, wherein said client has a communication interface means for communicating with said processor.

6. An apparatus according to claim 4, wherein said client is selected from the group consisting of a handheld computer, a personal computer, a cellular phone, and an eye diagnostic device having a communication interface.

7. An apparatus according to claim 1, wherein said processor is selected from the group consisting of a general purpose processor, an application specific integrated circuit, a digital signal processor, a programmable logic device, a microprocessor, a controller, a state machine, and an eye diagnostic device.

8. An apparatus according to claim 1, wherein said storage medium is integral to said processor.

9. An apparatus according to claim 1, wherein said calibration eye is selected from the group consisting of a surrogate eye and an eye of said individual.

10. The apparatus according to claim 1, wherein the portions of Newton's Rings comprise ring bundles.

11. A method for determining a glucose level of an individual, comprising:
calibrating intensity determinations of a plurality of portions of Newton's Rings in an eye with various glucose concentrations at multiple wavelengths;
lighting said individual's eye with a light source to create portions of Newton's Rings at said multiple wavelengths;
capturing captured images of a plurality of portions of Newton's Rings in said individual's eye at said multiple wavelengths;
processing the captured images to compensate for image capturing deviations between said calibrating step and said capturing step; and
determining various possible glucose concentrations based on intensity determinations of a plurality of portions of Newton's Rings in the processed captured images and the calibration results at said multiple wavelengths, and determining one common answer from the various possible glucose concentrations as said glucose level of said individual.

12. A process according to claim 11, wherein said calibrating step and said capturing step are performed at the same multiple wavelengths.

13. A process according to claim 11, wherein said lighting and capturing steps are performed with simultaneous multiple wavelengths.

14. A process according to claim 11, wherein said calibrating step is performed by calibrating said intensity determinations with various glucose concentrations in an eye selected from the group consisting of an eye of said individual and a surrogate eye.

15. The process according to claim 11, wherein the portions of Newton's Rings comprise ring bundles.

16. An apparatus for determining a glucose level of an individual having an eye, comprising:
a storage medium capable of containing a calibration table for said individual, said calibration table created by imaging a plurality of portions of Newton's Rings in said eye at multiple wavelengths and various glucose levels of said individual, using first base image parameters and said apparatus configured to store said calibration table in said storage medium prior to determining a glucose level of said individual;
a light source for lighting said eye at said multiple wavelengths to create portions of Newton's Rings;
an image capture device for capturing captured images of a plurality of portions of Newton's Rings in said eye at said multiple wavelengths using second base image parameters that approximate said first base image parameters;
an image processor connected to said storage medium and said image capture device for compensating said captured images for differences between said base image parameters; and
a dynamic pattern matcher connected to said image processor for comparing points on said compensated captured images of a plurality of portions of Newton's Rings to corresponding points in said calibration table at said multiple wavelengths to determine various possible concentration values for each wavelength, and for determining one common answer from the various possible concentration values as said glucose level of said individual.

17. An apparatus according to claim 16, wherein said points comprise "L" shaped phase detector areas.

18. An apparatus according to claim 16, wherein said points comprise "L" shaped phase detector areas defining an X area and a Y area, and said dynamic pattern matcher compares points by using the ratio Y/X of said phase detector areas or tracking the amplitude Y+X of said phase detector areas.

19. The apparatus according to claim 16, wherein the portions of Newton's Rings comprise ring bundles.

20. An apparatus according to claim 16, wherein said dynamic pattern matcher compares points by applying a Fourier transform.

* * * * *